United States Patent [19]

Hagarty

[11] Patent Number: 5,104,658
[45] Date of Patent: Apr. 14, 1992

[54] COLLAPSIBLE ARTHROPODICIDALLY-ACTIVE FOAM MATRIX AND METHOD OF MANUFACTURE

[75] Inventor: John D. Hagarty, Racine, Wis.

[73] Assignee: S. C. Johnson & Son, Inc., Racine, Wis.

[21] Appl. No.: 429,668

[22] Filed: Oct. 31, 1989

Related U.S. Application Data

[63] Continuation-in-part of Ser. No. 339,565, Apr. 17, 1989, abandoned, which is a continuation-in-part of Ser. No. 922,926, Oct. 24, 1986, Pat. No. 4,889,710, which is a continuation of Ser. No. 727,932, Apr. 26, 1985, abandoned.

[51] Int. Cl.$^5$ .................................. A01N 25/06
[52] U.S. Cl. ............................. 424/405; 424/43; 424/45; 424/409
[58] Field of Search .............. 424/405, 409, 45, 43

[56] References Cited

U.S. PATENT DOCUMENTS

| | | | |
|---|---|---|---|
| 2,754,243 | 7/1956 | Gysla et al. | 424/45 |
| 2,903,478 | 9/1959 | Lambrech | 424/45 |
| 3,042,703 | 7/1962 | Schegk et al. | 424/45 |
| 3,076,744 | 2/1963 | Geary | 424/45 |
| 3,111,539 | 11/1963 | Bocker | 424/45 |
| 3,244,586 | 4/1966 | Rigterink | 424/45 |
| 3,303,091 | 2/1967 | Marlander | 424/45 |
| 3,524,911 | 8/1970 | Leavitt | 424/45 |
| 3,591,662 | 7/1971 | Lorenz et al. | 424/45 |
| 3,716,600 | 2/1973 | Magee | 558/178 |
| 3,736,338 | 5/1973 | Gates et al. | 424/45 |
| 3,791,983 | 2/1974 | Maierson | 424/45 |
| 3,816,610 | 6/1974 | Lusby | 424/84 |
| 3,818,047 | 6/1974 | Henrick | 424/45 |
| 3,833,635 | 9/1974 | Henrick | 424/45 |
| 3,845,172 | 10/1974 | Magee | 424/45 |
| 3,865,874 | 2/1975 | Henrick | 562/582 |
| 3,970,584 | 7/1976 | Hart et al. | 424/45 |
| 4,286,020 | 8/1981 | Himel et al. | 428/407 |
| 4,439,342 | 3/1984 | Albanese | 424/43 |
| 4,889,710 | 12/1989 | Hagarty | 424/45 |

FOREIGN PATENT DOCUMENTS

| | | | |
|---|---|---|---|
| 596091 | 2/1961 | Belgium . | |
| 594669 | 3/1961 | Belgium . | |
| 1116656 | 11/1961 | Fed. Rep. of Germany . | |
| 2538470 | 8/1978 | Fed. Rep. of Germany . | |
| 45-11719 | 4/1970 | Japan | 424/45 |
| 48-10205 | 4/1973 | Japan | 424/43 |
| 48-10536 | 4/1973 | Japan | 424/45 |
| 54-23123 | 2/1979 | Japan | 424/45 |
| 57-64601 | 4/1982 | Japan . | |
| 8501876 | 5/1985 | PCT Int'l Appl. | 424/43 |
| 1107140 | 3/1968 | United Kingdom . | |

OTHER PUBLICATIONS

The Merck Index, 10th Edition, published 1983, Entry Nos. 25, 1035, 1766, 2167, 2968, 3125, 3470, 3910, 3927, 5111, 5150, 5859, 7251, 7372, and 7737.

Pesticides: Theory and Application by George W. Ware, published 1983.

McCutcheon's Emulsifiers and Detergents, pp. 244, 271, 272, and 287-290.

*Primary Examiner*—Lester L. Lee

[57] ABSTRACT

A novel arthropodicidally-active composition-of-matter is disclosed. Such a composition-of-matter comprises an aqueous lower alkanol solvent, and a toxicant as well as an emulsifier, both contained within the solvent. The amount of emulsifier, relative to the amount of solvent, is effective for forming a foam matrix that is able to collapse after a predetermined period of time thereby to form an arthropodicidally-active film. Also disclosed are methods for producing such an arthropodicidally-active film.

4 Claims, No Drawings

COLLAPSIBLE ARTHROPODICIDALLY-ACTIVE FOAM MATRIX AND METHOD OF MANUFACTURE (REFERENCE TO RELATED APPLICATIONS)

This new patent application is a continuation-in-part of my presently-pending U.S. application Ser. No. 339,565 filed 17 Apr. 1989 (now abandoned), which, in turn, is itself a continuation-in-part, of my U.S. application Ser. No. 922,926, now U.S. Pat. No. 4,889,710 filed 24 Oct. 1986, which is a continuation of my prior U.S. application Ser. No. 727,932 filed 26 Apr. 1985 (now abandoned), the benefit of which is now claimed for purposes of priority pursuant to 35 USC § 120.

TECHNICAL FIELD OF THE INVENTION

My present invention is generally directed to an arthropodicidally-active composition-of-matter and to its method of manufacture. My novel composition-of-matter, as formed initially, is characterized as a foam matrix. After a predetermined period of time, the foam matrix "breaks" (or "collapses"), thereby producing an arthropodicidally-active film. Still more particularly, my novel arthropodicidally-active composition-of-matter is water-soluble.

For purposes of my present invention, I shall use the term "arthropod", which is generally understood by those skilled in the art of "pest" control as connoting any member of a large group of invertebrate animals with jointed legs and segmented bodies. More particularly, I shall use this entomologically-known term, "arthropod", in its "generic" sense so as to include arachnids, crustaceans, insects, and myriapods.

BACKGROUND OF THE INVENTION

One's home is one's castle; and most people do not wish to share their castles with tiny, crawling pests such as ants, centipedes, pill bugs or spiders. Indeed, ridding one's home of small, crawling pests of these and other sorts can at times become a matter of concern, and effectively (i.e. totally) ridding one's home of such pests can thus pose a problem. Furthermore, with regard to any pesticide that is to be used in the home, the pesticidal activity as well as the physical appearance (of such a pesticidal composition) often plays an important role in a decision by today's consumers as to whether to purchase one particular pesticidally-effective product instead of that of another.

The amount of money spent annually on insect control by consumers is moreover sizable and generally well known; and there is a noticeable on-going quest for better, ever-more effective pesticides. Indeed, a wide variety of prior-art pesticidal compositions are well known.

For example, U.S. Pat. No. 3,816,610 to Lusby discloses a so-called "palatable", foamed rodent-control material. Such a "rodent-control" material, more particularly, is said to include a rodent control agent such as rodenticide which, in turn, is interspersed throughout a so-called "plastic foam cellular" structure. The plastic foam cellular structure is said to be produced by combining isocyanate with a mixture consisting of a polyol, a catalyst, a blowing agent, and a so-called "rodent-control" agent. Lusby discloses that such ingredients, after being thus-combined, react chemically and expand, up to fifty (50) or more times in volume, via so-called "foaming action". Lusby further discloses that the result of such a volume-expansion mechanism is the production of a low-density substance (or mass), such as a "foam", which is said to be able to fill up cavities and take their shape, whereupon such a mass quickly becomes rigid.

U.S. Pat. No. 3,524,911 to Leavitt discloses an insecticidal composition. More particularly, the Leavitt patent discloses that such an insecticidal composition, which is preferably utilized as an aerosol-sprayable composition, is characterized as being a so-called "substantially non-aqueous" mixture which is said to include a toxic concentration of a vaporizable insecticide as well as a so-called "substantially inert" foam-forming carrier. After this particular insecticidal composition is dispensed from its aerosol spray container, the foam-forming carrier is said to form a so-called "stable" (i.e. "form-sustaining") foam. Leavitt further discloses that the insecticide is released from such a foam carrier in toxic concentrations at a so-called "controlled" rate over a prolonged (or extended) period of time.

U.S. Pat. No. 3,970,584 to Hart et al., on the other hand, discloses a personal-care foam-forming emulsion that is utilized to produce a foam that is said to be "rich", "creamy", and "shiny". In particular, Hart et al. specifically teach that such a rich, creamy, shiny foam can be utilized to produce a variety of personal-care types of products. Still more particularly, Hart et al. specifically teach that such a rich, creamy, shiny foam can be utilized to produce an insect-repellent personal-care type of product.

Hart et al. thus specifically teach that their type of foam products can have certain "unique" characteristics which are said to be particularly desirable in the personal-care field. In this regard, Hart et al. particularly point out that their foam product will possess a so-called "fine" or "delicate" bubble structure, and that such a foam product will possess, as a result, certain desirable foam-density and foam-stiffness personal-care types of qualities. Hart et al. also specifically teach, however, that their particular foam products do not break down to form a film.

German Pat. ("Offenlegungsschrift") No. 25 38 470 discloses a method for producing a pesticidally-active composition-of-matter, characterized as an attractant in admixture with a toxicant, wherein the composition-of-matter is produced by a method whereby the attractant and toxicant are absorbed into a piece of plastic foam by so-called "electrostatic" forces.

U.S. Pat. No. 3,076,744 to Geary discloses an insecticidal bait composition which is said to include a so-called "polymerized aminoplast" as well as a so-called "insect-edible" attractant in admixture with an organic insecticide. The attractant and the insecticide, in turn, are said to be "molecularly occluded" within the polymerized aminoplast. Geary further discloses that the polymerized aminoplast, thus-containing the above-mentioned "occluded" ingredients, can be crushed to a fine-particle size and thereafter spread, for example, in insect-infested areas.

U.S. Pat. No. 3,791,983 to Maierson discloses so-called "aerosolizable" web-forming, sprayable compositions. Such compositions, in particular, are characterized as being self-supporting, three-dimensional webs of randomly-associated, joined monofilaments ranging in average diameter of from about 1 to 10 microns. Such so-called "web-forming" compositions are said to be utilizable for encapsulating certain insecticidal ingredients. Insecticidal ingredients, thus encapsulated, can then be used to combat insects.

U.S. Pat. No. 4,286,020 to Himel et al. also discloses a process for the encapsulation of insecticidal particles.

British Pat. No. 1,107,140 to Mitchell et al. discloses an insecticidally-active oil-in-water emulsion which, after being dispensed from an aerosol-type dispenser, preferably is so formulated as to produce a spray rather than a foam.

U.S. Pat. No. 4,456,587 to Keith discloses a so-called "pheromone delivery" system. In connection with such a system, one particular pheromone that is utilized as an attractant (in an insect trap) for a particular type of insect is contained within a polymeric film, wherein such a film is characterized as being relatively water-insoluble.

In view of the many features and advantages of the above-discussed prior-art pesticidal products as well as those prior-art pesticidal products which are presently commercially-available, present-day consumers nevertheless continue to seek ever-novel insecticidal compositions-of-matter for a variety of reasons. For example, a sizable population of the pesticide-purchasing public would like to be assured that a particular pesticidal composition is present at certain predetermined locations but would not like to be visually reminded of such a presence.

Further, easy clean-up and disposal of a variety of now-inactive pesticidal products is desirable. Pesticidally-active compositions are of course known, in general, to possess a finite activity period. To facilitate clean-up of compositions rendered pesticidally-inactive due to the passage of time, it would be desirable that such a pesticidally-active composition be water-soluble.

Still further, for the manufacturer of such a product, it would be desirable that the ingredients be relatively low-cost; and it would be even more desirable that such a product be relatively inexpensive to manufacture as well.

SUMMARY OF THE INVENTION

Accordingly, I have discovered a relatively low-cost method of preparing a novel pesticidally-active composition-of-matter. The three essential ingredients, moreover, are individually relatively low cost as well.

These three ingredients include (1) an aqueous lower alkanol solvent, (2) a toxicant, and (3) an emulsifier. My novel pesticidally-active composition-of-matter is characterized as a pesticidally-active surface coating or film. Such a film is produced by a method which comprises preparing a pesticidally-active composition-of-matter which, when formed initially, is characterized as a foam matrix. Such a foam matrix initially takes on a three-dimensional shape. However, a predetermined period of time after such a foam matrix is thus-formed, my pesticidally-active composition-of-matter is specifically so formulated as to "break" or collapse, thereby producing a pesticidally-active film.

Still further, and depending upon the relative amounts as well as the specific types of ingredients that are utilized in the manufacture of the novel pesticidally-active composition-of-matter of my present invention, such a film can be so formulated as to be pesticidally-active for weeks (or even months), as desired.

Furthermore, and as was briefly mentioned above, my novel composition-of-matter is water-soluble, a markedly desirable characteristic or feature, which enables easy clean-up and/or disposal of my novel composition-of-matter after it is rendered inactive due to the passage of time.

Moreover, my novel pesticidally-active composition-of-matter has been found to be suitable for controlling a wide variety of arthropods. For example, and depending upon the relative amounts and particular types of ingredients chosen, my novel composition-of-matter, as is shown hereinbelow, can specifically be so formulated as to be effective for controlling certain crustaceans (such as pill bugs or sow bugs), or certain arachnids (such as spiders), or a wide variety of certain well-known crawling insects (such as ants, cockroaches, earwigs, silverfish and the like), or certain myriapods (such as millipedes and centipedes), or certain combinations of these classes, i.e. arachnids, crustaceans, insects and myriapods (within the phylum "arthropoda").

Still further, and in accordance with certain general principles and features of my present invention, my novel composition-of-matter can specifically be so formulated as to be effective for killing a wide variety of arthropodic pests upon direct contact or upon ingestion (or both), as desired. In other words, there are certain specific formulations of my novel composition-of-matter which are effective so-called "contact-type" arthropodicides, whereas there are certain other specific formulations of my novel composition-of-matter which can be so formulated as to be arthropod-edible and which are thus effective arthropodicides upon ingestion by such pests.

My present invention is, accordingly, generally directed to an arthropodicidally-active composition-of-matter and to its method of manufacture. Such a composition-of-matter, as was briefly mentioned above, is characterized as including a specified aqueous lower alkanol solvent, and an emulsifier as well as a toxicant, each contained within the specified solvent. The amount of emulsifier, relative to the amount of solvent, is effective for purposes of forming a foam matrix that is able to "break" (or collapse) after a predetermined period of time. Such a foam matrix, moreover, is water soluble. The relative weight amounts of emulsifier and solvent, still further, are effective for causing such a foam matrix to thus "break" or collapse, after the predetermined period of time has passed, thereby producing an arthropodicidally-active water-soluble film. Furthermore, my novel composition-of-matter can specifically be so formulated such that the film is either transparent or translucent, as desired.

DETAILED DESCRIPTION OF THE PREFERRED EMBODIMENTS

While my present invention is susceptible to embodiment in various forms, there are hereinafter described, in detail, a variety of presently-preferred embodiments of my present invention. The detailed description presented hereinbelow is therefore to be considered as but an exemplification of my present invention without limitation to the various specific embodiments disclosed and discussed.

As was briefly previously mentioned, my present invention is generally directed to an arthropodically-active composition-of-matter and to its method of manufacture. Such a composition-of-matter is characterized as including an aqueous, lower-alkanol solvent such as a $C_1$ to $C_4$ alcohol solvent. The aqueous, lower-alkanol solvent is about 10 to about 60 parts-by-weight lower alkanol, preferably about 25 to about 50 parts-by-weight lower alkanol, and more preferably about 35 to about 45 parts-by-weight lower alkanol, based upon one-hundred (100) parts-by-weight of the arthropodicidally-active composition-of-matter of my present invention. A preferred lower alkanol is ethanol. (All numerical "parts" or percentages expressed herein shall refer to weight percentages, unless stated otherwise.) Water is generally present in an amount of about 25 to about 80 parts, preferably about 40 parts to about 60 parts, and more preferably about 45 parts to about 55 parts, based upon one-hundred (100) parts of the arthropodicidally-active composition-of-matter.

More particularly, my novel arthropodicidally-active composition-of-matter is characterized as further including an emulsifier as well as a toxicant, each contained within the aqueous, lower-alkanol solvent.

As an optional ingredient, my arthropodicidally-active composition-of-matter can further include an attractant.

Attractants suitable for purposes of inclusion in the composition-of-matter of my present invention are, moreover, generally well-known to those skilled in the art.

As was mentioned above, my novel composition-of-matter is initially characterized as a foam matrix that ultimately collapses to form a film. (Prior to formation of the foam matrix, the arthropodicidally-active composition-of-matter of my present invention is characterized as an oil-in-water emulsion.)

Any particular material that is (1) compatible with the film and (2) specifically attractive to a particular arthropod that is to be targeted for extermination or control may be employed as such an attractant. Accordingly, when employed for use against a particular arthropod, any edible material that is known to be particularly attractive to such an arthropod can of course be selected.

For sweet-loving ants and other sweet-loving insects such as cockroaches, for example, the edible attractant can be sucrose, fructose, glucose, maltose, honey, molasses, brown sugar, maple sugar, fruit syrup, corn syrup, maple syrup, and beet syrup, as well as pulverized raisins and other pulverized sweet fruits, if pulverization renders the particles sufficiently small.

In particular, one corn sweetener that is presently commercially available from Archer Daniels Midland Company (of Decatur, Ill.) under the "Corn Sweet 90" brand name and which includes about ninety (90) parts corn-derived fructose has been found to be particularly suitable in controlling various cockroaches. Other types of insects may prefer pulverized cereals, pulverized brans, or pulverized meals of various origin. Still other types of insects such as fire ants seem to prefer certain animal and/or vegetable oils and fats containing (or combined with) certain proteins.

As still further examples of such edible materials, there may be mentioned pulverized beef fat, pulverized bacon, pulverized fish meals and oils, pulverized eggs, pulverized meats, various pulverized meals, pulverized "tankage" (i.e., a known substance that is characterized as including about 50% protein, including meat scraps and bone scraps), butter, bacon drippings, lard, various pulverized vegetable protein extracts and hydrolyzates, pulverized dried brewer's solubles, pulverized tallow, pulverized cottonseed, pulverized soybean, pulverized corn, pulverized coconut, pulverized olive, pulverized palm, pulverized poppyseed, pulverized nuts, certain vegetable oils (such as soybean oil), various pulverized extracts (such as vanilla extract), and the like, as well as mixtures of these various attractants.

Such an attractant, which is (as was mentioned above) optional, may be employed in the arthropodicidally-active composition-of-matter in any desired proportion, generally ranging from about 0.1 parts to about 10 parts, preferably ranging from about 2 parts to about 8 parts, and more preferably ranging from about 4 parts to about 7 parts, per one-hundred (100) parts of the arthropodicidally-active composition-of-matter.

Toxicants suitable for purposes of inclusion in the composition-of-matter of my present invention are also well-known to those skilled in the art. Moreover, and as was also mentioned above, the pesticidally-active film can include a toxicant having a delayed effect (which has been found to be useful in controlling social insects such as ants), or the film can include a toxicant having an immediate effect (which has been found to be useful in controlling a wide variety of crawling arthropods). Such well-known toxicants include, but are not limited to, a variety of commercially-available organic compound-based toxicants, including organophosphorus compounds, and carbamates as well as inorganic toxicants and insect-growth regulators. (See, for example, "Pesticides: Theory and Application", by George W. Ware, published 1983 by W. H. Freeman and Company, hereby incorporated by reference.)

Accordingly, for purposes of my present invention, suitable organophosphorus compounds include certain phosphates, phosphonothionates, and phosphorothionates. For example, suitable, well-known organophosphorus compounds, useful as toxicants in the present invention, include, but are not limited to: acetylphosphoramidothioic acid O,S-dimethyl ester, also known by its so-called "trivial" name of Acephate, and commercially available under the "Ortho" and "Orthene" brand names (see also U.S. Pat. Nos. 3,716,600 and 3,845,172, both to Chevron); phosphorothioic acid O,O-diethyl O-(3,5,6-trichloro-2-pyridinyl) ester, also known by its trivial name of "Chlorpyrifos", and commercially available under the "Dursban", "Lorsban", and "Pyrinex" brand names (see also U.S. Pat. No. 3,244,586 to Dow); phosphorothioic acid O,O-diethyl O-[6-methyl-2-(1-methylethyl)-4-pyrimidinyl] ester, also known by its trivial name "Dimpylate", and commercially available under the "Basudin", "Diazinon", "Diazol", "Garden Tox", "Sarolex", and "Spectracide" brand names (see also U.S. Pat. No. 2,754,243 to Geigy); phosphorothioic acid O,O-dimethyl O-(3-methyl-4-nitrophenyl) ester, also known by its trivial name of "Fenitrothion", and commercially available under the "Accothion", "Cyfen", "Cyten", "Folithion", "MEP", "Metathion", and "Sumithion" brand names (see also Belgian Pat. No. 594,669 to Sumitomo and Belgian Pat. No. 596,091 to Bayer); phosphorothioic acid O,O-dimethyl O-[3-methyl-4-(methylthio)phenyl] ester, also known by its trivial name of "Fenthion", and commercially available under the "Baycid", "Baytex", "Entex", "Lebaycid", "Mercaptophos", "Queletox", "Spotton", "Talodex", and "Tiguvon" brand names (see also German Pat. No. 1,116,656 as well as U.S. Pat. No. 3,042,703, both to Bayer; see also Japanese Pat. No. 15,130, which issued in 1964 to Sumitomo); 4-ethoxy-7-phenyl-3,5-dioxa-6-aza-4-phosphaoct-6-ene-8-nitrile 4-sulfide, also known by its trivial name of "Phoxim", and commercially available under the "Baythion", "Sebacil", and "Volaton" brand names (see also U.S. Pat. No. 3,591,662 to Bayer); and the O,O-dimethyl analog of O-[2-(diethylamino)-6-methyl-4-pyrimidinyl] phosphorothioic acid O,O-diethyl ester, also known by its trivial name of "Pirimiphos-methyl", and commercially available under the "Actellic", "Blex", and "Silo San" brand names. (See, e.g., entry numbers 25, 2167, 2968, 3910, 3927, 7251 and 7372, respectively, in "The Merck Index", 10th ed., published in 1983 by Merck & Co., Inc.)

For purposes of further elucidating the various principles and aspects of my present invention, suitable carbamates include, but are not limited to: 2,2-dimethyl-1,3-benzodioxol-4-ol methylcarbamate, also known by its trivial name of "Bendiocarb", and commercially available under the "Ficam" brand name (see also U.S. Pat. No. 3,736,338 to Fisons); 1-naphthalenol methylcarbamate, also known by its trivial name of "Carbaryl", and commercially available under the "Arylam", "Carylderm", "Dicarbam", "Seffein", and "Sevin" brand names (see also U.S. Pat. No. 2,903,478 to Union Carbide); and 2-(1-methylethoxy)phenol methylcarbamate, also known by its trivial name of "Propoxur", and commercially available under the "Baygon", "Bifex", "Blattanex", "InvisiGard", "Propyon", "Sendran", "Suncide", and "Unden" brand names (see also U.S. Pat. No. 3,111,539 to Bayer). See, e.g., entry Nos. 1035, 1766 and 7737, respectively, in "The Merck Index", 10th ed.

For purposes of still further elucidating the various principles and aspects of my present invention, suitable inorganic toxicants include, but are not limited to, various well-known stomach poisons, such as the "arsenicals" (i.e., any one of a variety of well-known arsenic-containing compounds), certain heavy metal-containing compounds, and certain fluorine-containing compounds, as well as boric acid, silica gel and sodium borate. (See, e.g., page 62 of "Pesticides: Theory and Application" by George W. Ware.)

Insect-growth regulators (IGRs), occasionally referred to by those skilled in the art as "biorationals", are rather specific chemicals which are presently believed to be generally environmentally "safe". Moreover, certain ones of the presently-known IGRs tend to closely resemble certain biological, organic-type chemicals produced by certain insects and/or plants.

IGRs are known to function by altering the growth and development of a wide assortment of arthropods. The observed effects of IGRs upon metamorphosis, upon reproduction, upon behavior and upon embryonic, larval and nymphal development have moreover been reported in the literature. (See, e.g., page 62 of "Pesticides: Theory and Application" by George W. Ware.) A number of IGRs, found to be effective when utilized in very minute quantities, appear to have no undesirable effects on humans and wildlife. (Id.) Furthermore, it is well known that IGRs are typically non-specific; and as a result, they are known to affect not only the target species of arthropod but also a variety of other arthropods as well. (Id.)

Accordingly, for purposes of my present invention, suitable insect growth regulators (IGRs) include, but are not limited to: N-[[(4-chlorophenyl)amino]carbonyl]-2,6-difluorobenzamide (a known chitin-synthesis inhibitor), also known by its trivial name of "Diflubenzuron", and commercially available under the "Difluron" and "Dimilin" brand names; 2,3,14,22,25-pentahydroxycholest-7-en-6-one ($C_{27}H_{44}O_6$) and 2,3,14,20,22,25-hexahydroxycholest-7-en-6-one ($C_{27}H_{44}O_7$), also known by their trivial names of "alpha-Ecdysone" and "beta-Ecdysone", respectively, which are well-known insect-molting hormones that are used for the purpose of controlling the pupation of a wide variety of insects; 7-ethyl-9-(3-ethyl-3-methyloxiranyl)-3-methyl-2,6-nonadienoic acid methyl ester ($C_{18}H_{30}O_3$) and cis-10,11-epoxy-3,7,11-trimethyl-trans,trans-2,6-tridecadienoic acid methyl ester ($C_{17}H_{28}O_3$), both generally described by the trivial term "Juvenile Hormone" (JH), each more particularly recognized (by those skilled in the art) by the abbreviations "C-18 JH" and "C-17 JH", respectively; 3,7,11-trimethyl-2,4dodecadienoic acid 2-propynyl ester, also known by its trivial name of "Kinoprene", and commercially available under the "Enstar" brand name (see also U.S. Pat. No. 3,833,635 to Zoecon); and 11-methoxy-3,7,11-trimethyl-2,4-dodecanoic acid 1-methylethyl ester, also known by its trivial name of "Methoprene", and commercially available under the "Altosid", "Apex", "Kabat", and "Manta" brand names (see also U.S. Pat. Nos. 3,818,047 and 3,865,874, both to Zoecon). (See, e.g., entry Nos. 3125, 3470, 5111, 5150 and 5859, respectively, in "The Merck Index", 10th ed.; and pages 62–64 of "Pesticides: Theory and Application" by G. W. Ware.) The term "Juvenile Hormone", as used in this application, includes: the so-called "JH mimic" (JHM) and "JH analog" (JHA) IGRs, as well as their broader synonyms, the so-called "juvenoids" and "juvegens". (See, e.g., page 62 of "Pesticides: Theory and Application" by Ware.)

Still further, and in addition to what was specifically identified hereinabove, there are certain other well-known toxicants which are particularly effective in controlling a variety of arthropods (except certain ants), in general, and which are suitable for purposes of the present invention. Such toxicants include, but are not limited to, cypermethrin, certain other synthetic pyrethroids (such as permethrin, deltamethrin, alphamethrin, and cyphenothrin and the like), and natural pyrethrum. Natural pyrethrins, sold as 20 weight percent actives, are commercially available from the so-called "Py Board" of Kenya. One such synthetic pyrethroid, known by its brand name of "Cyfluthrin", is commercially available from Mobay Chemical Corp. of Pittsburgh, Pa. Furthermore, and as was briefly parenthetically noted immediately above, most pyrethroids—which have been observed as being repellent to most ants, in general, at even minute concentrations—would of course not be included in the formulations of my novel composition-of-matter when such is to be used to control ants. (Cyfluthrin, as the data appearing further hereinbelow suggests, is one exception.)

Such toxicants, suitable for purposes of my present invention, may be employed in my arthropodicidally-active composition-of-matter in any desired proportion, generally ranging from about 0.01 parts to about 5.0 parts, preferably ranging from about 0.25 parts to about 1.25 parts, and more preferably ranging from about 0.5 parts to about 1 part, per one-hundred (100) parts of my novel arthropodicidally-active composition-of-matter.

One particularly suitable toxicant, well-known by its brand name of "Sulfluramide" and characterized as a fluorinated sulfonamide, is commercially available from the Griffin Corporation of Valdosta, Ga.

As still other optional ingredients, the novel arthropodicidally-active composition-of-matter of my present invention can further include a foam-matrix stabilizer or a foam-matrix de-stabilizer, a film stabilizer, an emulsion stabilizer, or any combination of such stabilizers, as desired. Stabilizers of these sorts are well known to those skilled in the art.

As was briefly mentioned above, one characteristic of my present invention is that it is an arthropodicidally-active composition-of-matter which, when formed initially, is a foam matrix. Prior to formation of such a foam matrix, the arthropodicidally-active composition-of-matter of my present invention is, moreover, characterized as an "oil-in-water" emulsion (i.e., a so-called "water-out" emulsion).

More particularly, such a composition-of-matter, as was also briefly mentioned above, includes an emulsifier in its aqueous, lower-alkanol solvent. The emulsifier is preferably of the so-called "nonionic" charge type. The amount of emulsifier in the solvent is effective for forming a foam matrix that is able to collapse after a predetermined period of time. For example, and depending on the relative amounts of ingredients that are utilized in forming one particular arthropodicidally-active composition-of-matter which is in accordance with the principles of my present invention, such a foam matrix is generally able to "break" or collapse into an arthropodicidally-active film within a range of about 3 seconds to about 2 minutes. Further, the relative amounts of emulsifier and aqueous, lower-alkanol solvent are so chosen as to be effective for causing the thus-formed foam matrix to collapse after passage of the predetermined time period, for thereby forming the arthropodicidally-active film. Thus, by design, the foam matrix is specifically formulated to be an "unstable" foam.

My arthropodicidally-active composition-of-matter can, moreover, be readily dispensed from various types of known dispensing systems and equipment—e.g., from spray guns, portable aerosol containers, cans and the like—to provide an advantageous way of applying the arthropodicidally-active composition-of-matter of my present invention into a variety of void spaces including, but not limited to, cracks and crevices, beneath doors and around windows, along the underside surfaces of countertops, tables and chairs, and in pipe, drains, and other conduit.

Prior to formation of the above-discussed foam matrix, the arthropodicidally-active composition-of-matter of my invention is characterized (as was briefly mentioned above) as a so-called "water-out" emulsion (i.e., an oil-in-water emulsion). Suitable emulsifiers (or surfactants), in accordance with the principles of my present invention include, but are not limited to, certain ones of the so-called "block polymers", the so-called "ethoxylated alcohols", the so-called "ethoxylated alkyl phenols", the so-called "ethoxylated amines" (and/or "amides"), the so-called "ethoxylated" and "propoxylated" fatty acids, the so-called "ethoxylated fatty esters" (and "oils") as well as the "fatty esters", the so-called "glycerol esters" and "glycol esters" as well as the lecithins (and the lecithin derivatives), the so-called "monoglycerides" (and their derivatives), certain phosphate derivatives as well as certain phosphate esters, the so-called "sorbitan" derivatives, and the so-called "sucrose esters" (and their derivatives). Emulsifiers of these types are commercially available and are well known to those skilled in the art. (See, e.g., pages 287-290 of the 1986 North American Edition of "McCutcheon's Emulsifiers & Detergents", published by the McCutcheon Division of the MC Publishing Co. of Glen Rock, N.J.) One particularly suitable emulsifier, well-known by its brand name of "Triton X-100" and characterized as a liquid nonionic octylphenoxy polyethoxy ethanol having an HLB (hydrophile-lipophile balance) value of 13.5, is commercially available from Rohm & Haas Company of Philadelphia, Pa. Yet another particularly suitable emulsifier, well-known by its brand name of "Triton X-193" and characterized as a liquid nonionic/anionic blend, is also commercially available from Rohm & Haas Co. Still another particularly suitable emulsifier, well-known by its brand name of "APG 500" and characterized as a glycoside, is commercially available from Horizon Chemical, a division of Staley Continental Incorporated of Decatur, Ill. Yet another particularly suitable emulsifier, well-known by its brand name of "Span 20" and characterized as a non-ionic, liquid sorbitan monolaurate having an HLB value of 8.6, is commercially available from ICI Americas, Incorporated, of Wilmington, Del.

The emulsifier is generally present in an amount of about 0.10 parts to about 5 parts, preferably about 0.5 parts to about 2 parts, and more preferably about 0.75 parts to about 1.5 parts, per one-hundred (100) parts of my novel, foamable arthropodicidally-active composition-of-matter.

In addition to the above-discussed optional attractant ingredient, the foamable arthropodicidally-active composition-of-matter of my present invention can further optionally include a propellant for causing the emulsifier-containing arthropodicidally-active composition-of-matter (which is characterized as an "oil-in-water" emulsion) to produce the unstable, arthropodicidally-active foam matrix. The unstable foam matrix of my present invention is thus able to collapse, after passage of the above-mentioned predetermined period of time, thereby forming an arthropodicidally-active film. Such a film, as was also briefly mentioned above, is water-soluble.

When the foamable, water-soluble, arthropodicidally-active composition-of-matter of my present invention further includes the optional propellant ingredient, the propellant is generally present in an amount of about 5 parts to about 25 parts, preferably about 10 parts to about 15 parts, and more preferably about 8 parts to about 12 parts, based upon one-hundred (100) parts of the propellant-containing, foamable, arthropodicidally-active composition-of-matter of my present invention.

Normally, the optional propellant ingredient is so chosen as to be immiscible with the aqueous phase; but it need not be. In particular, certain water-soluble propellants, such as dimethyl ether (DME), are suitable for purposes of my present invention. Additional suitable water-soluble or partially water-soluble propellants include nitrous oxide (which is moderately soluble in water), as well as carbon dioxide (which is soluble in water in only very minute concentration).

Additional suitable propellants, for purposes of my present invention, include, but are not limited to, certain liquefied and compressed gases. Suitable liquefied gases, for purposes of my present invention, include a wide variety of known hydrocarbon propellants (such as various $C_1$ to $C_4$ hydrocarbons) and certain halogenated propellants (such as the various commercially-available halogenated propellants collectively known in the art generally as "Freon").

Illustrative of the preferred hydrocarbon propellants are propane, n-butane, isobutane, and various mixtures thereof. Additional suitable compressed gases, for purposes of the present invention, include air and nitrogen.

One well-known presently preferred propellant, often referred to as "A-46" by those skilled in the art, has a vapor pressure of about 46 pounds per square inch gauge (psig) and comprises about 80 mole percent isobutane and about 20 mole percent propane. Another well-known presently preferred propellant, referred to as "A-31" by those skilled in the art, is isobutane.

In addition to the above-identified ingredients, the arthropodicidally-active composition-of-matter of my present invention can further optionally include a fragrance, a microorganism growth inhibitor (or so-called "preservative"), and/or a metal-corrosion inhibitor. One such illustrative microorganism growth inhibitor (or preservative) is formaldehyde. It can well be appreciated by those skilled in the art that inclusion of a preservative and/or a metal-corrosion inhibitor may be desirable, for a variety of reasons. One particularly suitable preservative, well-known by its brand name of "Kathon", is commercially available from Rohm & Haas Co. The arthropodicidally-active composition-of-matter of my present invention can still further optionally include a disinfectant agent, and/or a dye (or a pigment) to thus produce a "colored" film, if desired.

Illustrative of a suitable metal-corrosion inhibitor, for purposes of my present invention, is a compound selected from the group consisting of sodium benzoate, sodium nitrite, and the combination that is characterized as including both sodium benzoate and sodium nitrite.

My present invention will now be described in even greater detail by reference to the following Examples which are presented hereinbelow for illustrative purposes only and which are thus not intended to limit the scope of my present invention whatsoever.

| Example I: One Collapsible Foam | | |
|---|---|---|
| Ingredients | Function | Parts |
| Water | Carrier | 44.50 |
| Ethanol (95%) | Solvent | 40.00 |
| A-31 | Propellant | 10.00 |
| Maltose | Attractant | 4.00 |
| Triton X-100 | Emulsifier | 1.00 |
| Dursban | Toxicant | 0.50 |

Procedure For Making the Collapsible Foam of Example I

The arthropodicidally-active collapsible foam of Example I was produced as follows.

A weighed quantity of ethanol (95%) solvent was introduced into a beaker of suitable size equipped with a stirrer. [The term "ethanol (95%)", as used in connection with Example I (above) and subsequent examples, is understood to mean 95 weight percent ethyl alcohol and 5 weight percent water.] A weighed quantity of toxicant was then combined with the beaker-contained solvent, utilizing moderate agitation, while slowly heating to above room temperature (about 25 degrees Celsius). Next, a weighed quantity of emulsifier was incorporated into the beaker-contained ingredients, still utilizing moderate agitation and slowly heating the beaker contents to about 45° C. until a homogeneous solution was obtained.

Separately, a weighed quantity of water was introduced into another beaker of suitable size, also equipped with a stirrer. A weighed quantity of attractant was then combined with the beaker-contained water, also utilizing moderate agitation, while slowly heating to about 45° C. until a second homogeneous solution was obtained.

Next, both solutions were combined together, utilizing moderate agitation to produce a mixture. The resultant mixture was then introduced into a container, pressurized with a weighed quantity of propellant; and the container was then sealed.

| Example II: Another Collapsible Foam | | |
|---|---|---|
| Ingredients | Function | Parts |
| Water | Carrier | 49.29 |
| Ethanol (95%) | Solvent | 40.00 |
| A-31 | Propellant | 10.00 |
| APG 500 | Emulsifier | 0.50 |
| Cyfluthrin | Toxicant | 0.11 |
| Kathon | Preservative | 0.10 |

Procedure For Making the Collapsible Foam of Example II

In the preparation of the collapsible foam of Example II the procedures of Example I were substantially followed, except that (1) the solvent-based solution further included a weighed quantity of preservative but no attractant, (2) "APG 500" was used as the emulsifier in place of "Triton X-100", and (3) "Cyfluthrin" was used as the toxicant in place of "Dursban".

| Example III: Yet Another Collapsible Foam | | |
|---|---|---|
| Ingredients | Function | Parts |
| Water | Carrier | 49.29 |
| Ethanol (95%) | Solvent | 40.00 |
| A-31 | Propellant | 10.00 |
| Triton X-193 | Emulsifier | 0.50 |
| Cyfluthrin | Toxicant | 0.11 |
| Kathon | Preservative | 0.10 |

Procedure For Making the Collapsible Foam of Example III

In the preparation of the collapsible foam of Example III the procedures of Example II were substantially followed, except that "Triton X-193" was used in place of "APG 500" as the emulsifier.

| Example IV: Still Another Collapsible Foam | | |
|---|---|---|
| Ingredients | Function | Parts |
| Water | Carrier | 47.90 |
| Ethanol (95%) | Solvent | 40.00 |
| A-31 | Propellant | 10.00 |
| APG 500 | Emulsifier | 1.00 |
| Sulfluramide | Toxicant | 1.00 |
| Kathon | Preservative | 0.10 |

Procedure For Making the Collapsible Foam of Example IV

In the preparation of the collapsible foam of Example IV the procedures of Example II were substantially followed, except that "Sulfluramide" was used in place of "Cyfluthrin" as the toxicant and a commercially available homogenizer was used, after all ingredients were combined, to blend the ingredients.

Arthropodicidal Activity

The collapsible foams of Examples I and II were tested for effectiveness against ants, centipedes, earwigs, firebrats (similar to silverfish), German cockroaches (*Blattella germanica*), harvestmen (commonly known as "daddy-longlegs"), millipedes, sowbugs, spiders, and ticks.

For each of Examples I and II, there was 100 percent mortality for each type of arthropod recited immediately hereinabove, upon introduction of each such arthropod, 4 hours following, and 24 hours following foam-matrix collapse to form a residual film.

Effectiveness Procedure

A sufficient number of cylindrical, open-top containers, each measuring about 8 centimeters (cm) in diameter by about 8.5 cm deep were obtained. An amount of collapsible foam was then sprayed into each such cylindrical container, from an aerosol container for a time period of about 0.5 seconds from a distance of about 30 cm. The container discharge rate for the foam of Example I was about 1.85 grams (g) per sec.; and the container discharge rate for the foam of Example II was about 1.90 g per sec. After about 8 seconds (sec.), the foam of Example I was observed to collapse to thus form a residual film; and after about 5 sec., the foam of Example II was similarly observed to collapse to thus form a residual film.

A "treatment" is defined as testing the effectiveness of each such residual film, at a specified time period after formation of such film, for a particular arthropod. With respect to each of the above-recited anthropods (except for the harvestmen), each such treatment was performed twice. The above mortality data, therefore, is the average of two such replicates, except for the harvestmen mortality data which consisted of only one replicate.

What has been described herein is a novel arthropodicidally-active composition-of-matter, and methods for producing the same. While my present invention has been described with reference to certain preferred embodiments, it is to be understood that my present invention is not to be limited to the preferred embodiments discussed herein. On the contrary, alternatives, changes and/or modifications will become apparent to those skilled in the art upon reading the foregoing description. Accordingly, such alternatives, changes and/or modifications are to be considered as forming a part of my present invention insofar as such fall within the spirit and scope of the appended claims.

I claim:

1. An arthropodicidally-active composition-of-matter comprising:

10 to 60 parts-by-weight of an aqueous $C_1$ to $C_4$ lower alkanol solvent;

a toxicant contained within the solvent; and an effective amount of an emulsifier also contained within the solvent and present in an amount of at least 0.5 parts-by-weight, for forming a foam matrix that is able to collapse into a film after about 3 seconds to about 2 minutes subsequent to formation of the foam matrix, thereby forming an arthropodicidally-active film, wherein the arthropodicidally-active film is characterized as being water-soluble, and wherein the arthropodicidally-active composition-of-matter is further characterized as being an oil-in-water emulsion prior to formation of the foam matrix.

2. The arthropodicidally-active composition-of-matter of claim 1 wherein the aqueous lower alkanol solvent additionally contains an attractant.

3. The arthropodicidally-active composition-of-matter of claim 1 wherein the lower alkanol is ethanol.

4. The arthropodicidally-active composition-of-matter of claim 1 further comprising a propellant.

* * * * *